US00PP37197P2

(12) United States Plant Patent
Graff

(10) Patent No.: US PP37,197 P2
(45) Date of Patent: Jan. 6, 2026

(54) ***MANDEVILLA* PLANT NAMED 'QD-36'**

(50) Latin Name: *Mandevilla sanderi*
Varietal Denomination: QD-36

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 19/240,756

(22) Filed: Jun. 17, 2025

(51) Int. Cl.
*A01H 5/02* (2018.01)
*A01H 6/08* (2018.01)

(52) U.S. Cl.
USPC ..... Plt./232
CPC ..... *A01H 6/088* (2018.05); *A01H 5/02* (2013.01)

(58) Field of Classification Search
USPC ..... Plt./232
CPC . A01H 5/02; A01H 5/00; A01H 6/088; A01H 6/08
See application file for complete search history.

(56) References Cited

U.S. PATENT DOCUMENTS

PP32,505 P2 * 11/2020 Graff ..... A01H 6/088 Plt./232

* cited by examiner

*Primary Examiner* — June Hwu
(74) *Attorney, Agent, or Firm* — C. Anne Whealy

(57) ABSTRACT

A new and distinct cultivar of *Mandevilla* plant named 'QD-36', characterized by its compact and broadly upright plant habit; freely branching habit; dense and bushy appearance; dark green-colored leaves; freely flowering habit; and bright red-colored flowers that are held beyond the foliar plane.

3 Drawing Sheets

Figure 1:
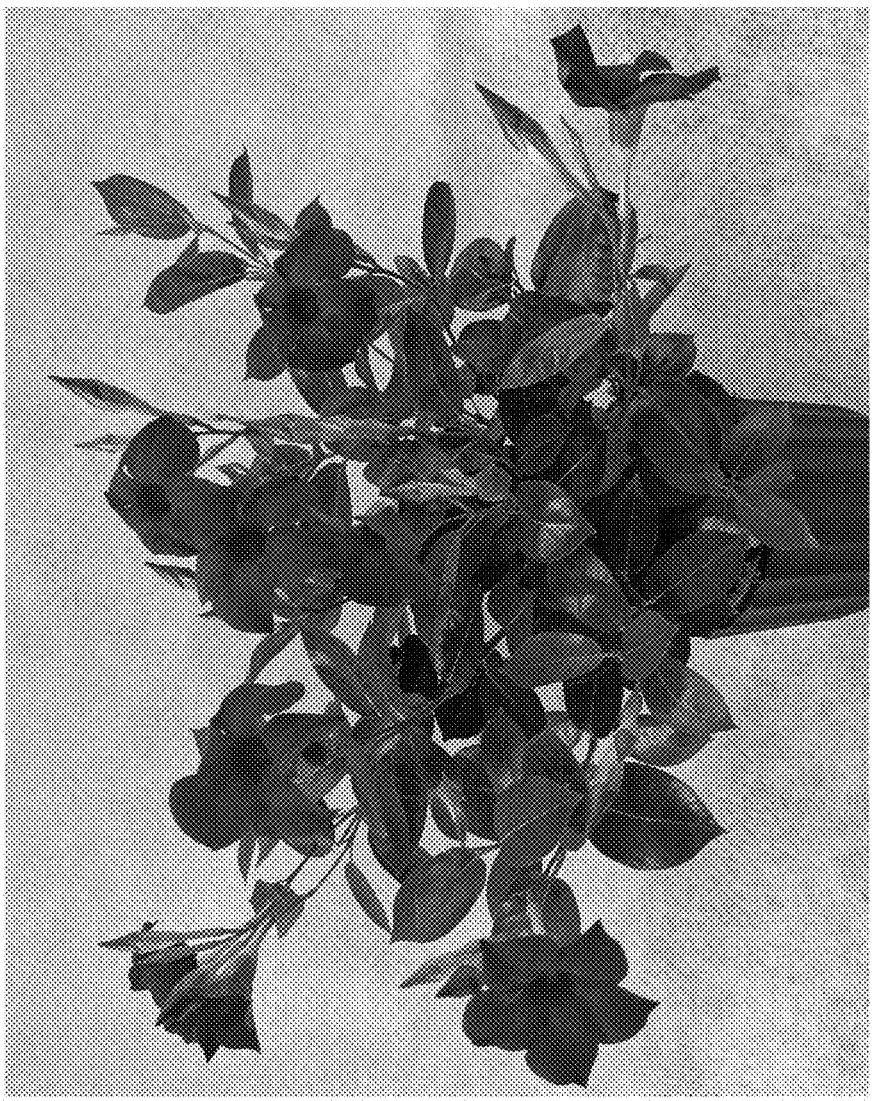

Botanical designation: *Mandevilla sanderi.*
Cultivar denomination: 'QD-36'.

CROSS-REFERENCED TO CLOSELY-RELATED APPLICATION

A European Community Plant Breeder's Rights application for the instant plant was filed by the Assignee of the instant application, Graff Breeding A/S of Sabro, Denmark on Apr. 16, 2025, application number 2359472. Foreign priority is not claimed to this European Plant Breeder's Rights application.

BACKGROUND OF THE INVENTION

The present invention relates to a new and distinct cultivar of *Mandevilla* plant, botanically known as *Mandevilla sanderi* and hereinafter referred to by the name 'QD-36'.

The new *Mandevilla* plant is a product of a planned breeding program conducted by the Inventor in Sabro, Denmark. The objective of the breeding program is to create new compact and freely branching *Mandevilla* plants with numerous attractive flowers.

The new *Mandevilla* plant originated from an open-pollination in Sabro, Denmark in August, 2016 of a proprietary selection of *Mandevilla sanderi* identified as code number GB 2013-0902, not patented, as the female, or seed, parent with an unknown proprietary selection of *Mandevilla sanderi* as the male, or pollen, parent. The new *Mandevilla* plant was discovered and selected by the Inventor as a single flowering plant from within the progeny of the stated open-pollination in a controlled greenhouse environment in Sabro, Denmark in May, 2017.

Asexual reproduction of the new *Mandevilla* plant by cuttings in a controlled greenhouse environment in Sabro, Denmark, since September, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'QD-36'. These characteristics in combination distinguish 'QD-36' as a new and distinct *Mandevilla* plant:

1. Compact and broadly upright plant habit.
2. Freely branching habit; dense and bushy appearance.
3. Dark green-colored leaves.
4. Freely flowering habit.
5. Bright red-colored flowers that are held beyond the foliar plane.

Plants of the new *Mandevilla* can be compared to plants of the female parent selection. Plants of the new *Mandevilla* differ primarily from plants of the female parent selection in flower color as plants of the new *Mandevilla* have bright red-colored flowers whereas plants of the female parent selection have soft pink-colored flowers.

Plants of the new *Mandevilla* can also be compared to plants of *Mandevilla hybrida* 'QD8', disclosed in U.S. Plant Pat. No. 32,505. In side-by-side comparisons, plants of the new *Mandevilla* differ primarily from plants of 'QD8' in the following characteristics:

1. Plants of the new *Mandevilla* are more compact than plants of 'QD8'.
2. Stems of plants of the new *Mandevilla* are glossier than stems of plants of 'QD8'.
3. Plants of the new *Mandevilla* have larger and glossier leaves than plants of 'QD8'.
4. Plants of the new *Mandevilla* have longer leaf petioles than plants of 'QD8'.
5. Plants of the new *Mandevilla* have smaller flowers than plants of 'QD8'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'QD-36' grown in a container.

Figure 2:
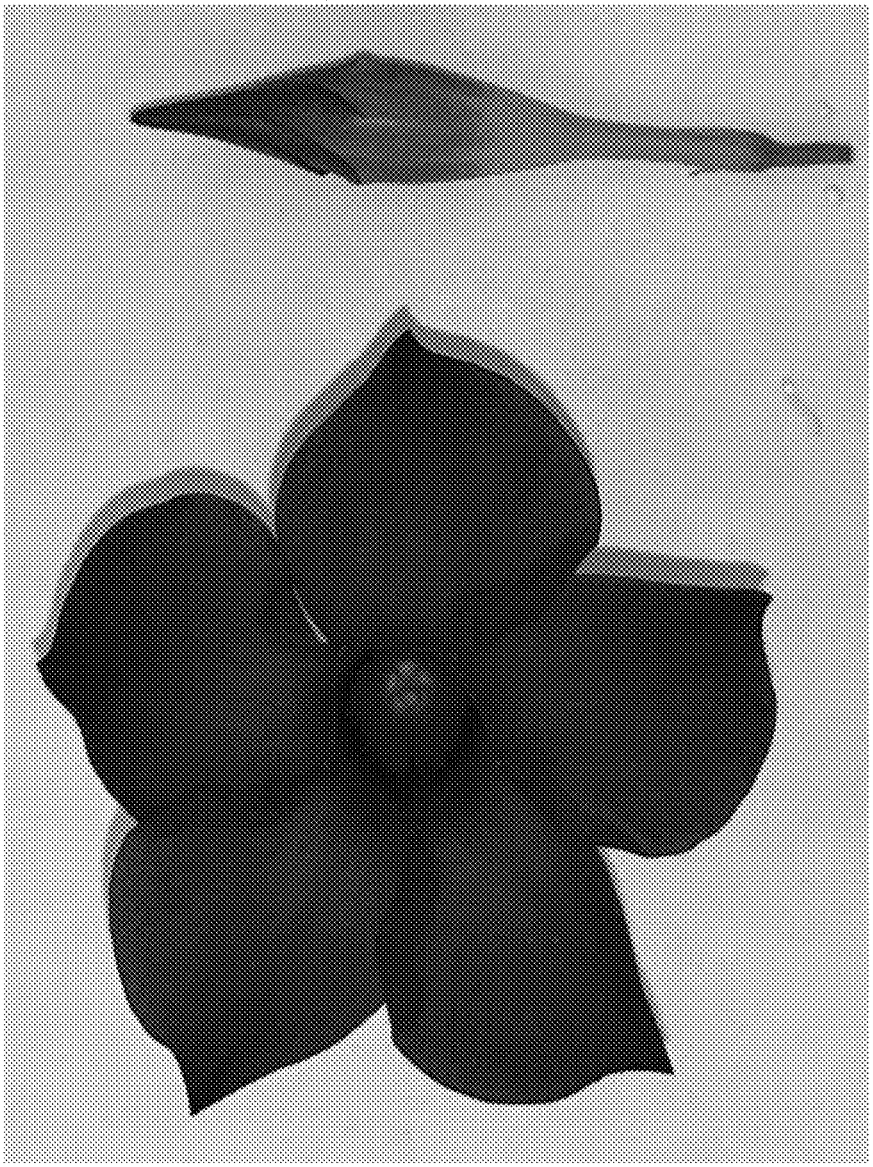

The photograph on the second sheet (FIG. 2) is a close up view of a typical open flower and flower bud of 'QD-36'.

Figure 3:
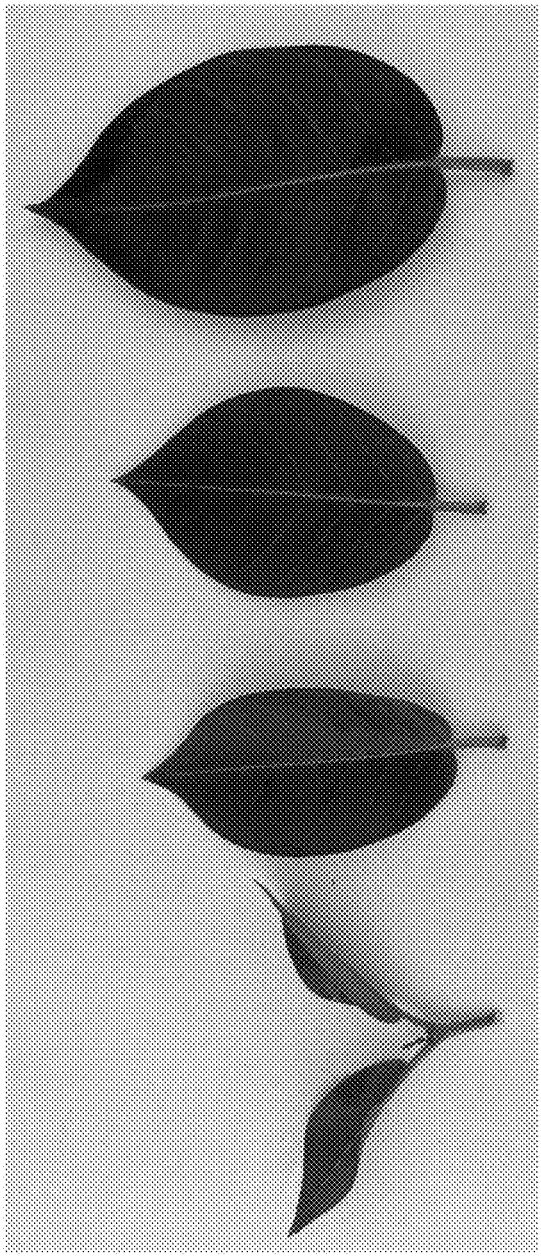

The photograph on the third sheet (FIG. 3) is a close up view of typical developing and fully developed leaves of 'QD-36'.

DETAILED BOTANICAL DESCRIPTION

The aforementioned photographs and following observations, measurements and values describe plants grown during the summer in 13-cm containers in a glass-covered greenhouse in Sabro, Denmark and under cultural practices typical of commercial *Mandevilla* production. During the production of the plants, day temperatures ranged from 20° C. to 25° C., night temperatures ranged from 19° C. to 21° C. and light levels ranged from 40 klux to 50 klux. Plants were pinched two times and were 31 weeks old when the photographs and description were taken. In the following description, color references are made to The Royal Horticultural Society Colour Chart, 2001 Edition, except where general terms of ordinary dictionary significance are used.

Botanical classification: *Mandevilla sanderi* 'QD-36'.

Parentage:

*Female, or seed, parent*.—Proprietary selection of *Mandevilla sanderi* identified as code number GB 2013-0902, not patented.

*Male, or pollen, parent*.—Unknown proprietary selection of *Mandevilla sanderi*, not patented.

Propagation:

*Type*.—By vegetative cuttings.

*Time to initiate roots, summer*.—About three weeks at soil and ambient temperatures about 21° C.

*Time to initiate roots, winter*.—About four weeks at soil and ambient temperatures about 21° C.

*Time to produce a rooted young plant, summer*.—About seven weeks at soil and ambient temperatures about 21° C.

*Time to produce a rooted young plant, winter*.—About eight weeks at soil and ambient temperatures about 21° C.

*Root description*.—Fine, fibrous; typically close to 161C in color, actual color of the roots is dependent on substrate composition, water quality, fertilizers, substrate temperature and physiological age of roots.

*Rooting habit*.—Freely branching; dense.

*Tubers*.—Tuber formation has been observed on plants older than one year.

Plant description:

*Plant and growth habit*.—Compact and broadly upright plant habit; overall plant shape is broadly obovate; relatively moderately vigorous to vigorous growth habit and moderate growth rate; freely branching habit; dense and bushy appearance.

*Plant height, soil level to top of foliar plane*.—About 20 cm to 25 cm.

*Plant height, soil level to top of floral plane*.—About 25 cm to 30 cm.

*Plant diameter* (*spread*).—About 25 cm to 35 cm.

*Lateral branch description*.—Branching habit: Freely branching habit, about three to five primary lateral branches each with typically three to five secondary lateral branches developing per plant. Length: About 12 cm to 20 cm. Diameter: About 5 mm. Internode length: About 3 cm to 5 cm. Aspect: Upright to outwardly. Strength: Strong. Texture and luster: Smooth, glabrous; glossy; becoming woody with development. Color, developing: Close to 144A. Color, developed: Close to 144A; when woody, becoming closer to 148A and 199A.

Leaf description:

*Arrangement*.—Opposite, decussate; simple.

*Length*.—About 6 cm to 7 cm.

*Width*.—About 4 cm to 5 cm.

*Shape*.—Elliptic.

*Apex*.—Acuminate.

*Base*.—Rounded to cordate.

*Margin*.—Entire.

*Texture and luster, upper surface*.—Smooth, glabrous; coriaceous; glossy.

*Texture and luster, lower surface*.—Smooth, glabrous; coriaceous; matte.

*Venation pattern*.—Pinnate.

*Color*.—Developing leaves, upper surface: Close to 137A. Developing leaves, lower surface: Close to 147B. Full expanded leaves, upper surface: Close to 139A; venation, close to 137C. Fully expanded leaves, lower surface: Close to 146A; venation, close to 137A.

*Petioles*.—Length: About 1.5 cm. Diameter: About 2 mm to 3 mm. Strength: Moderately strong to strong. Texture and luster, upper and lower surfaces: Smooth, glabrous; semi-glossy to matte. Color, upper surface: Close to 144A. Color, lower surface: Close to 144B.

Flower description:

*Flower type and flowering habit*.—Single salverform flowers arranged singly or in terminal or axillary racemes; flowers rounded star-shaped and face upright to outwardly; freely flowering habit with about three to four flower buds and about one to two open flowers per inflorescence; about 40 to 50 flowers develop during the flowering season.

*Natural flowering season*.—Plants flower continuously from spring into the autumn in Denmark; plants begin flowering about nine to twelve weeks after the final pinch.

*Flower longevity on the plant*.—About 8 to 14 days; flowers persistent.

*Fragrance*.—None detected.

*Inflorescence height* (*before flowers open*).—About 4 cm to 7 cm.

*Inflorescence diameter* (*before flowers open*).—About 5 cm to 7 cm.

*Flower buds*.—Length: About 6 cm to 7 cm. Diameter: About 1.5 cm. Shape: Rhomboidal. Texture and luster: Smooth, glabrous; slightly glossy. Color: Close to 53B and 145C.

*Flowers*.—Appearance: Flared trumpet, petals fused and five-parted; petals slightly imbricate. Diameter: About 8 cm. Depth (length): About 2.5 cm. Throat diameter: About 2 cm. Tube length: About 2 cm. Tube diameter: About 5 mm.

*Petals*.—Quantity and arrangement: Five petals arranged in a single whorl; proximally, petals are fused into a funnelform tube. Petal length: About 3 cm to 4 cm. Petal width: About 3.5 cm. Petal shape and appearance: Unequal spatulate to fan- shaped. Petal apex: Acute. Petal margin: Entire; not undulate. Petal texture and luster, upper and lower surfaces: Smooth, glabrous; velvety; matte. Throat texture: Smooth, glabrous; velvety; matte. Tube texture: Smooth, glabrous; matte. Color: Petal, when opening, upper surface: Close to 46A to 46B. Petal, when opening, lower surface: Close to 53B. Petal, fully opened, upper surface: Close to 46B; venation, close to 53B; color does not change with subsequent development. Petal, fully opened, lower surface: Close to 53B; venation, close to 52B; color does not change with subsequent development. Throat: Close to N172B; venation, close to N172A. Tube: Close to 145B; venation, close to 145B.

*Sepals*.—Quantity and arrangement: Five sepals arranged in a single whorl. Sepal length: About 1 cm. Sepal width: About 2 mm to 5 mm. Sepal shape: Lanceolate. Sepal apex: Acuminate. Sepal base: Rounded. Sepal margin: Entire. Sepal texture and luster, upper and lower surfaces: Smooth, glabrous; semi-glossy. Sepal color: When opening, upper and lower surfaces: Close to 145A. Fully opened, upper and lower surfaces: Close to 145B.

*Peduncles*.—Length: About 4 cm. Diameter: About 2 mm to 4 mm. Strength: Strong. Aspect: Mostly upright. Texture and luster: Smooth, glabrous; semi-glossy. Color: Close to 144A.

*Pedicels*.—Length: About 1.5 cm. Diameter: About 2 mm to 3 mm. Strength: Strong. Texture and luster: Smooth, glabrous; semi-glossy. Color: Close to 144B.

*Reproductive organs*.—Stamens: Quantity and arrangement: Typically five; basifixed; anthers connivent. Filament length: About 1 mm to 3 mm. Filament color: Close to 11C. Anther size: About 3 mm by 7 mm. Anther shape: Linear. Anther color: Close to 162C. Pollen amount: Moderate. Pollen color: Close to 162C. Pistils: Quantity: Typically one. Pistil length: About 2 cm. Style length: About 2 cm. Style color: Close to 193B. Stigma diameter: About 3 mm. Stigma shape: Rounded to deltoid. Stigma color: Close to 144A; at the apex, close to 137A. Ovary color: Close to 144B.

*Fruits and seeds*.—To date, fruit and seed development has not been observed on plants of the new *Mandevilla*.

Pathogen & pest resistance: To date, plants of the new *Mandevilla* have not been observed to be resistant to pathogens and pests common to *Mandevilla* plants.

Temperature tolerance: Plants of the new *Mandevilla* have been observed to tolerate temperatures of about 10° C. to 44° C. and to be suitable for USDA Hardiness Zones 10B through 13.

It is claimed:

1. A new and distinct *Mandevilla* plant named 'QD-36' as herein illustrated and described.

* * * * *